(12) United States Patent
Jorabchi et al.

(10) Patent No.: US 9,966,243 B2
(45) Date of Patent: May 8, 2018

(54) APPARATUS AND METHODS FOR PLASMA-ASSISTED REACTION CHEMICAL IONIZATION (PARCI) MASS SPECTROMETRY

(71) Applicant: GEORGETOWN UNIVERSITY, Washington, DC (US)

(72) Inventors: Kaveh Jorabchi, Arlington, VA (US); Haopeng Wang, Ellicott City, MD (US)

(73) Assignee: Georgetown University, Washington, DC (US)

( * ) Notice: Subject to any disclaimer, the term of this patent is extended or adjusted under 35 U.S.C. 154(b) by 221 days.

(21) Appl. No.: 14/764,047

(22) PCT Filed: Jan. 28, 2014

(86) PCT No.: PCT/US2014/013428
§ 371 (c)(1),
(2) Date: Jul. 28, 2015

(87) PCT Pub. No.: WO2014/120676
PCT Pub. Date: Aug. 7, 2014

(65) Prior Publication Data
US 2016/0013037 A1    Jan. 14, 2016

Related U.S. Application Data

(60) Provisional application No. 61/758,238, filed on Jan. 29, 2013, provisional application No. 61/930,342, filed on Jan. 22, 2014.

(51) Int. Cl.
*G01N 30/90* (2006.01)
*H01J 49/00* (2006.01)
(Continued)

(52) U.S. Cl.
CPC ...... *H01J 49/0031* (2013.01); *G01N 30/7206* (2013.01); *G01N 30/7233* (2013.01);
(Continued)

(58) Field of Classification Search
USPC .................. 73/23.37, 35.08, 114.67, 861.09
See application file for complete search history.

(56) References Cited

U.S. PATENT DOCUMENTS 4,833,294 A * 5/1989 Montaser ................. H05H 1/30
219/121.48
5,012,052 A * 4/1991 Hayes ................ G01N 30/7206
250/282

(Continued)

FOREIGN PATENT DOCUMENTS

EP       1 726 946       11/2006

OTHER PUBLICATIONS

International Search Report issued in corresponding PCT International Application No. PCT/US2014/013428 and the Written Opinion.
(Continued)

*Primary Examiner* — Eric S McCall
*Assistant Examiner* — Mohammed E Keramet-Amircolai
(74) *Attorney, Agent, or Firm* — Klarquist Sparkman, LLP

(57) ABSTRACT

Plasma-assisted reaction chemical ionization (PARCI) provides highly sensitive elemental analysis by producing positively and negatively charged ions. The PARCI apparatuses, kits, and methods described in this application relate to systems that comprise a chemical reaction interface (CRI) containing reactant gas plasma and an ionization chamber that is downstream from the CRI. The ionization chamber facilitates formation of ions from element-specific products of the CRI by an electron source or an ionization gas. In
(Continued)

particular, PARCI provides a method for conducting highly sensitive mass spectrometric elemental analysis of analyte compounds with high ionization potential elements; for example, fluorine, chlorine, and bromine.

44 Claims, 12 Drawing Sheets

(51) Int. Cl.
  *H01J 49/10* (2006.01)
  *H01J 49/14* (2006.01)
  *G01N 30/72* (2006.01)
  *H01J 49/04* (2006.01)

(52) U.S. Cl.
  CPC ............ *H01J 49/04* (2013.01); *H01J 49/105* (2013.01); *H01J 49/145* (2013.01)

(56) References Cited

U.S. PATENT DOCUMENTS

| | | | |
|---|---|---|---|
| 6,355,416 B1 * | 3/2002 | Abramson | C12Q 1/68 435/6.12 |
| 7,394,065 B2 | 7/2008 | Grimm, II et al. | |
| 2001/0004102 A1 * | 6/2001 | Shiokawa | H01J 49/145 250/288 |
| 2005/0196871 A1 | 9/2005 | Cody et al. | |
| 2006/0249672 A1 * | 11/2006 | Grimm, II | H01J 49/165 250/288 |
| 2013/0082172 A1 * | 4/2013 | Syage | H01J 49/049 250/288 |

OTHER PUBLICATIONS

Examination Report issued by European Patent Office for EPC Application No. 14745930.9 dated Jul. 26, 2017, 5 pages.

* cited by examiner 100 nM injections, 50 µL/min, 20 µL loop

APPARATUS AND METHODS FOR PLASMA-ASSISTED REACTION CHEMICAL IONIZATION (PARCI) MASS SPECTROMETRY

CROSS REFERENCE TO RELATED APPLICATIONS

This application claims the benefit of priority of U.S. Provisional Application No. 61/758,238, filed Jan. 29, 2013 and U.S. Provisional Application No. 61/930,342, filed Jan. 22, 2014.

Any foregoing applications and all documents cited therein or during their prosecution ("application cited documents") and all documents cited or referenced in the application's cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention Citation or identification of any document in this application is not an admission that such document is available as prior art to the present invention.

FIELD OF THE INVENTION

This invention relates to the field of elemental mass spectrometry, and in particular, Chemical Reaction Interface Mass Spectrometry (CRIMS). Apparatuses, kits, and methods for the formation and detection of both positively and negatively charged ions formed in CRIMS are provided. As an illustration, this invention can be applied to the analysis of chemicals found in medicine, pharmaceuticals, biotechnologies, agriculture, and other areas of research.

BACKGROUND

Fields such as biochemistry, geochemistry, nutrition, organic chemistry, physiology, and pharmacology, use elemental analysis in a variety of applications. (See Griffin, I. J., *J. Anal. At. Spectrom.* 2002, 17, 1186-1193.) Elemental mass spectrometry offers a sensitive and relatively simple approach for quantitative analysis. Elemental mass spectrometry works by breaking the molecules into their constituent atoms, and then providing a constant response factor for each element, regardless of the chemical structure of compounds. Therefore, quantitative concentration measurements, as well as isotope ratio analysis, can be performed in the absence of individual standards for compounds of interest. Further, using elemental mass spectrometry, isotopic labeling patterns may be exploited to identify a geographic origin of a sample, to study a drug's metabolism (See Branch et al., *J. Anal. At. Spectrom.* 2003, 18, 17-22), or to monitor levels of biological compounds. (See Jorabchi et al., *Anal. Chem.* 2005, 77, 5402-5406.)

Chemical Reaction Interface Mass Spectrometry (CRIMS) is an example of a technique used in elemental mass spectrometry. CRIMS provides an analytical method for the selective detection of elements or isotopes from chemical and biological analytes. In particular, quantitative and isotopic analysis of compounds with high molecular weight, for example biological proteins, is hindered by the complexity of spectra and mass limits of mass spectrometry. CRIMS works by breaking molecules, especially large molecules into elemental constituents, which can readily be detected by a mass spectrometer. By breaking apart larger molecules, CRIMS provides a simple method to monitor the elemental content, and thereby the concentration of molecules and isotopic signature of elements. The ability of CRIMS to analyze large molecular analytes has advantages in fields that require the analysis of large non-volatile chemicals.

In conventional CRIMS, an analyte is introduced into a low pressure and high temperature plasma gas, referred to as the chemical reaction interface (CRI). Within the plasma, an analyte reacts with a reactant gas, breaking the chemical structure of the analyte into small and stable element specific reaction products. For illustration, elements present in an analyte, such as carbon, nitrogen, and bromine are liberated as $CO_2$, $NO_2$, and HBr (when hydrogen atoms are present). Sulfur may be converted to $SO_3$, $SO_4$, and $HSO_4$ (when hydrogen atoms are present) upon reaction of analyte with oxygen.

The elemental reaction products from the plasma stream are then ionized, which allows their identification and quantification by mass spectrometry. Traditionally, ionization is performed via electron impact after the products are transferred to a high vacuum region in the mass spectrometer. Methods such as electron impact generally limit efficient ionization to positive ion formation, limiting the utility of CRIMS in detecting negative ions. Further, the high-vacuum requirement of electron impact limits the analyte throughput into the ion source. This leads to loss of sensitivity in CRIMS as majority of the analyte stream coming out of the reaction interface is pumped away to reduce the pressure.

Elements such as fluorine cannot be readily quantified by detecting positively charged ions due to high ionization potential. Yet current estimates state that 20% of drugs and 30% of agrochemicals contain fluorine. Current techniques for halogen-specific detection in gas chromatography (GC) and liquid chromatography (LC) primarily focus on the use of plasma emission spectroscopy and plasma mass spectrometry as detectors. These techniques rely on positive ion generation or excitation of halogens. But considering the high ionization potential of certain elements, e.g., halogens, these techniques are not efficient.

There is demand in the field for elemental mass spectrometric analysis that can efficiently generate ions without a loss of sensitivity by, for example, allowing for the detection of negatively charged ions and/or facilitating ionization at higher pressures.

SUMMARY OF THE INVENTION

The present invention comprises apparatuses, kits, and methods for conducting plasma-assisted reaction chemical ionization (PARCI) for elemental analysis of chemical and biological compounds. In an aspect of this invention, PARCI comprises a chemical reaction interface (CRI) plasma cavity and an ionization chamber. In an embodiment, the ionization chamber is downstream from the plasma cavity. In certain embodiments, positive and/or negative ions are capable of being produced in the ionization chamber. In certain embodiments, the ionization chamber contains an electron source. In certain embodiments, the ionization chamber contains an ionization gas and/or a dopant.

As described herein, PARCI allow for the production and detection of both positive and negative ions from analytes in Chemical Reaction Interface Mass Spectrometry (CRIMS). In certain embodiments, positive and negative ions of the present invention may be produced at plasma gas pressure by introducing an ionization gas downstream of the CRI plasma cavity and into the stream of reaction products. In certain embodiments, the ionization gas reacts with metastable species from the plasma to produce positively and/or negatively charged ionization reagents.

In an embodiment of PARCI, the stream of reaction products contains carrier gas, metastable species of the carrier gas, and an unreacted part of the reaction gas. This stream is then mixed with ionization gas or a dopant to induce ionization. In an embodiment of the invention, an excited metastable species of the carrier gas may form upon exposure to the plasma cavity. In an embodiment, the ionization potential of the ionization gas is less than the ionization potential of the carrier gas. In an embodiment, the ionization potential of the ionization gas is less than the energy level of the metastable species of the carrier gas.

In certain embodiments, the ionization chamber comprises a dopant molecule that reacts with metastable species from the plasma to produce positively and/or negatively charged ionization reagents. In certain embodiments, both an ionization gas and a dopant molecule are present in the ionization chamber. In an embodiment, the ionization potential of the dopant is less than the ionization potential of the carrier gas. In an embodiment, the ionization potential of the dopant is less than the energy level of the metastable species of the carrier gas.

The introduction of an ionization gas and/or a dopant downstream of the plasma cavity allows a PARCI system to produce both positive and negative ions from the element specific products from the analyte. As an additional advantage of certain embodiments, the ionization step at plasma gas pressure eliminates the losses associated with transfer of neutrals into conventional high-vacuum ion source.

In certain embodiments, negative ions may be produced by an electron source in the ionization chamber. In an embodiment of this invention, the electron source is an independent electron source. Examples of independent electron sources include beta emitters, electric discharges, and photoionization of a dopant molecule.

In an embodiment, the present invention relates to the formation of negatively charged element specific products. In certain embodiments the negatively charged atoms may be produced at low pressure. In other embodiments, the negatively charged atoms may be produced at atmospheric pressure.

As an aspect of PARCI, elements of high ionization potential can be quantified by mass spectrometry. Accordingly, the present invention includes methods for conducting mass spectrometric analysis on molecules containing high ionization potential elements. High ionization potential elements may be found in molecules that are relevant to a variety of fields, including environmental contaminants, pharmaceuticals, biological compounds, and natural products. In certain embodiments, the present invention provides methods of conducting elemental analysis on organohalogens.

In an embodiment, the present invention provides an apparatus for elemental mass spectrometry comprising:
  a chemical reaction interface (CRI), which comprises reactant gas plasma;
  an ionization chamber,
    wherein the ionization chamber is downstream of the CRI;
    and
  a mass-spectrometer.

In another embodiment, the present invention provides an apparatus for elemental mass spectrometry comprising:
  a chemical reaction interface (CRI) comprising reactant gas plasma,
    wherein the pressure in the CRI is greater than about 1 torr;
  an ionization chamber,
    wherein the ionization chamber is downstream of the CRI, and wherein the pressure in the ionization chamber is greater than about 1 torr; and
  a mass-spectrometer.

In certain embodiments of the above-described apparatus, positive or negatively charged atoms and/or element-specific molecules are produced in the ionization chamber. In other embodiments, negatively charged atoms are produced in the ionization chamber. In certain embodiments, the ionization chamber comprises an ionization gas, a dopant, and/or an electron source.

In another embodiment, the present invention provides an apparatus for elemental mass spectrometry comprising:
  a chemical reaction interface (CRI) comprising reactant gas plasma;
  an ionization chamber comprising an ionization gas, a dopant, and/or an electron source; and
  a mass-spectrometer.

In certain embodiments of the above-described apparatus, positive or negatively charged atoms and/or element-specific molecules are produced in the ionization chamber. In other embodiments, negatively charged atoms are produced in the ionization chamber.

In another embodiment, an apparatus for conducting Chemical Reaction Interface Mass Spectrometry (CRIMS) is provided, wherein the apparatus contains means for introducing a dopant molecule downstream of the Chemical Reaction Interface (CRI) plasma cavity.

In an embodiment, the present invention provides a method for elemental mass spectrometric analysis of an analyte comprising:
  (1) introducing a sample comprising the analyte into a sample introduction component of a mass spectrometric system;
  (2) transporting the analyte into a chemical reaction interface (CRI) comprising a reactant gas plasma;
    wherein the CRI converts the analyte into one or more element specific compounds;
  (3) ionizing the element specific compounds to form charged element specific products; and
  (4) detecting the one or more charged element specific products by a mass spectrometer.

In another embodiment, the present invention provides a method for elemental mass spectrometric analysis of an analyte comprising:
  (1) introducing a sample comprising the analyte into a sample introduction component of a mass spectrometric system;
  (2) transporting the analyte into a chemical reaction interface (CRI) comprising a reactant gas plasma;
    wherein the CRI converts the analyte into one or more element specific compounds, and
    wherein the pressure in the CRI is greater than about 1 torr;
  (3) ionizing the element specific compounds in an ionization chamber,
    wherein the pressure in the ionization chamber is greater than about 1 torr,
  (4) detecting the one or more charged element specific products by a mass spectrometer.

In certain embodiments of the above-described method, positive or negatively charged atoms and/or element-specific molecules are produced in the ionization chamber. In other embodiments, negatively charged atoms are produced in the ionization chamber. In certain embodiments, the ionization chamber comprises an ionization gas, a dopant, and/or an electron source.

In another embodiment, the present invention provides a method for elemental mass spectrometric analysis of an analyte comprising:
(1) introducing a sample comprising the analyte into a sample introduction component of a mass spectrometric system;
(2) transporting the analyte into a chemical reaction interface (CRI) comprising a reactant gas plasma; wherein the CRI converts the analyte into one or more element specific compounds;
(3) ionizing the element specific compounds in an ionization chamber comprising an ionization gas, a dopant, and/or an electron source,
(4) detecting the one or more charged element specific products by a mass spectrometer.

In certain embodiments of the above-described apparatus, positive or negatively atoms and/or element-specific molecules are produced in the ionization chamber. In other embodiments, negatively charged atoms and/or element-specific molecules are produced in the ionization chamber.

In another aspect of the invention, a kit is provided that allows the conversion of an atmospheric-pressure sampling mass spectrometer instrument (such as LC-MS) into a PARCI instrument capable of producing positive and/or negative ions for analysis. In an embodiment, the kit allows the conversion of a mass spectrometer into a PARCI apparatus as described in the foregoing.

In an embodiment, the kit comprises a sample introduction system for plasma-assisted reaction chemical ionization (PARCI) comprising:
means for introducing a sample comprising an analyte into the sample introduction system;
a chemical reaction interface (CRI) comprising a plasma cavity;
wherein the plasma cavity comprises a plasma of a carrier gas with a reactant gas;
an ionization chamber comprising an ionization gas, a dopant, and/or an electron source downstream from the CRI; and
means for coupling the kit with mass spectrometer.

In an embodiment, the above-identified kit provides for a CRI that is at a pressure of greater than about 1.0 torr. In an embodiment, the above-identified kit provides for an ionization chamber that is at a pressure of greater than about 1.0 torr.

In an embodiment, comprises a means for introducing ionization gas or dopant into the ionization chamber.

DETAILED DESCRIPTION OF THE INVENTION

Figure 1:
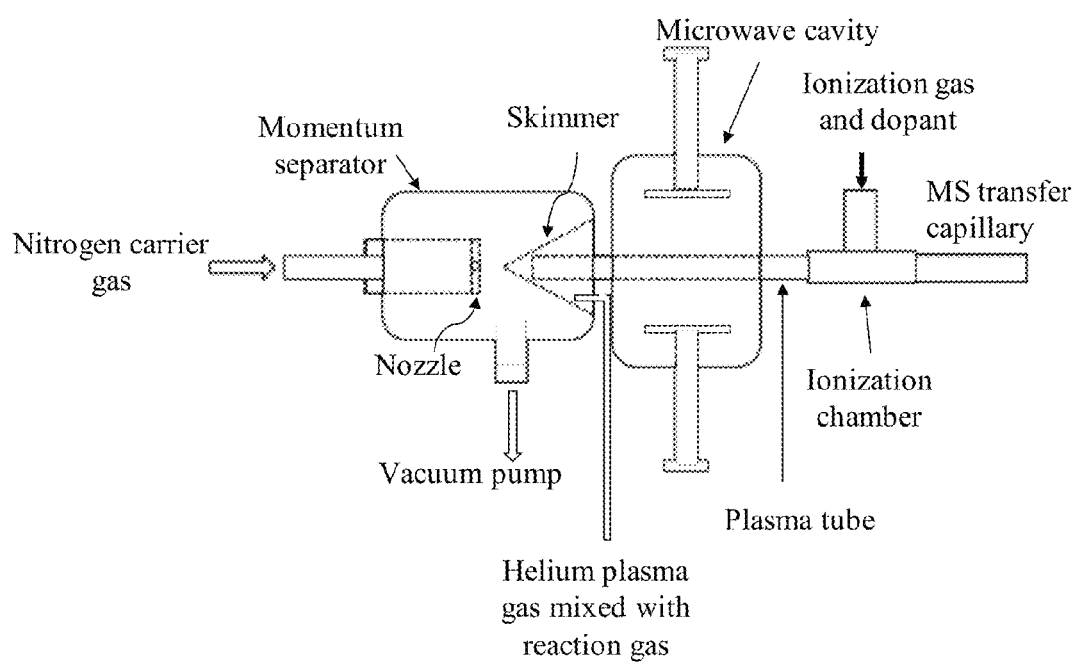
FIG. 1: A schematic diagram of the PARCI apparatus for Chemical Reaction Interface Mass Spectrometry comprising means for introducing a dopant molecule and/or ionization gas downstream of the Chemical Reaction Interface (CRI) plasma cavity.

The present invention provides for chemical reaction interface mass spectrometry (CRIMS), wherein it is possible to form and detect both negative and positive ions, which is referred to herein as plasma-assisted reaction chemical ionization (PARCI). Like CRIMS, PARCI is a method for quantitative isotopic measurement of elements in chemical compounds. In particular, PARCI provides a method for the quantitative and isotopic measurement of chemical elements found in analytes, including, but not limited to, organic chemical compounds, polymers, amino acids, polypeptides, proteins, carbohydrates, nucleic acids, and lipids.

While CRIMS methods in the art generally provide for positive ion formation, PARCI provides a means of overcoming this limitation and providing for the production and analysis of both positively and negatively charged ions. Accordingly, PARCI represents a superior technique for conducting elemental analysis of high ionization potential elements.

Embodiments of PARCI described herein may also allow for improved sensitivity. PARCI allows for ionization of elemental products at a pressure that is similar to the chemical reaction interface (CRI) plasma. This avoids the need for high-vacuum and loss of elemental products. Embodiments of PARCI described herein may also allow the use of atmospheric pressure sampling mass spectrometers for conducting CRIMS, and overcoming sensitivity limitations of the conventional high-vacuum electron impact source.

In PARCI, a sample containing one or more analytes is introduced into a mass spectrometric system. Once an analyte has been isolated from the sample, it travels to a chemical reaction interface (CRI), which comprises a plasma cavity containing plasma and reactant gasses, where the analyte is decomposed into element specific reaction products.

In an embodiment of PARCI, an ionization chamber is downstream from the CRI. In an embodiment, the ionization chamber is suitable for producing both positively and negatively charged element specific product ions. In certain embodiments, the pressure of the CRI is greater than about 1.0 torr. In certain embodiments, the pressure of the ionization chamber is greater than about 1.0 torr. In certain embodiments, the ionization chamber may contain an ionization gas, a dopant, and/or an electron source.

In an embodiment of PARCI an ionization gas and/or a dopant is introduced into the flow of products downstream of the plasma cavity. It is believed that metastable and high energy species from the plasma react with the ionization gas and/or dopant to create positive and negative ionization reagents. These charged ionization reagents can then interact with, and ionize the element specific products produced in the CRI.

In another embodiment of PARCI an electron source is introduced into the flow of products downstream of the plasma cavity. The electron source can ionize the element specific products to form negative elemental ions.

In an embodiment, a sample containing one or more analytes may be introduced to a chromatographic system in order to separate the analytes from the sample. The chromatographic step allows for the separation of one or more analytes of interest in a sample via a chromatographic column. In an embodiment, the chromatographic step may include liquid chromatography or gas chromatography. In a particular embodiment, the chromatographic step is liquid chromatography. In a specific embodiment, the chromatographic step is high performance liquid chromatography (HPLC).

Following liquid chromatography, it is another aspect of the present invention to provide for the nebulization of an analyte solution coming from the liquid chromatograph. Nebulizers that may be used include, but are not limited to, thermospray nebulizers (TSN) and pneumatic high efficiency nebulizers (HEN). (See Jorabchi, et al., *Anal. Chem.* 2005, 77, 5402-5406.)

Solvent flow rate coming out of a liquid chromatographic towards a chemical reaction interface may also be adjusted. One of ordinary skill in the art may make adjustments to provide for optimum flow rates. In certain embodiments, the flow rate is less than or equal to 1.0 mL/min. In certain embodiments, the flow rate is between about 1.0 µL/min and 1.0 mL/min; about 1.0 µL/min and 0.5 mL/min; about 1.0 µL/min and 0.25 mL/min; about 1.0 µL/min and 100 µL/min; about 10.0 µL/min and 1.0 mL/min; about 10.0 µL/min and 0.5 mL/min; about 10.0 µL/min and 0.250 mL/min; about 10.0 µL/min and 100 µL/min; about 50.0 µL/min and 1.0 mL/min; about 50.0 µL/min and 0.5 mL/min; about 50.0 µL/min and 0.250 mL/min; or about 50.0 µL/min and 100 µL/min.

After the chromatographic step, an analyte solution may be introduced into a chemical reaction interface (CRI). For example, analytes that have been separated by gas chromatography may proceed directly to the chemical reaction interface. But if one or more analytes in a solution, for example following a liquid chromatographic separation, the solvent may have to be removed.

In certain embodiments, a liquid sample transported from a liquid chromatographic system must first be "dried" to remove the solvents from the analyte. In an embodiment, the present invention comprises a means to separate the analyst from solvent. In an embodiment, the solvent is removed from the sample by use of a system comprising a nebulizer, spray chamber, heater, condenser, and/or a membrane desolvator to remove solvents from the sample.

A momentum separator may be used to introduce analyte particles into the CRI cavity. A momentum separator is a means of enriching the sample by selecting the central part of a spray with a set of orifices and/or skimmers, where particles with a higher momentum diverge less from the spray, and thus are separated from the solvent resulting the enrichment of the sample (See P. C. Winkler, et al., *Anal. Chem.*, 1988, 60, 489.)

In the present invention, the CRI is a plasma cavity where the analyte decomposes into constituent elements. In an embodiment, the CRI is a microwave induced plasma, an inductively coupled plasma, a glow discharge plasma, or a capacitively coupled plasma.

In the CRI, analyte particles react with a reactant gas. In an embodiment, the reactant gas may be separately infused into the carrier or plasma gas. In another embodiment, the reactant gas is a residual gas or solvent in the carrier gas.

Elements from the analyte are quantitatively converted into a mixture of elemental specific products. In certain embodiments, the microwave-induced plasma gas comprises one or more reactant gasses selected from helium (He), nitrogen ($N_2$), argon (Ar), oxygen ($O_2$), hydrogen ($H_2$), water ($H_2O$), and atmospheric air.

In an embodiment, the plasma cavity is maintained in a pressure range between about 1 torr to about 50 torr; about 1 torr to about 20 torr; about 5 torr to about 50 torr; or about 5 torr to about 20 torr. In an embodiment, the plasma cavity is maintained at a pressure range of greater than about 0.1 torr, 0.5 torr, 1.0 torr, 10 torr, 50 torr, 100 torr, 250 torr, or 500 torr. In another embodiment, the plasma cavity is maintained at atmospheric temperature.

In an embodiment, the ionization chamber is maintained in a pressure range between about 1 torr to about 50 torr; about 1 torr to about 20 torr; about 5 torr to about 50 torr; or about 5 torr to about 20 torr. In an embodiment, the ionization chamber is maintained at a pressure range of greater than about 0.1 torr, 0.5 torr, 1.0 torr, 10 torr, 50 torr, 100 torr, 250 torr, or 500 torr. In another embodiment, the ionization chamber is maintained at atmospheric temperature.

After the elemental reaction products are formed, the products travel downstream where ionization gas and/or dopant molecules are introduced to the elemental reaction product stream (FIG. 1). The dopant molecule reacts with metastable species from the plasma at a pressure close to that of plasma to produce charged ionization reagents. The reaction products are then ionized in the presence of the charged ionization reagents to form a charged reaction product. The charged reaction products may then be detected by a mass spectrometer.

In certain embodiments, the ionization step is conducted near plasma gas pressure, which eliminates the losses associated with transfer of neutrals into conventional high-vacuum ion source. In some embodiments, the ionization step may be conducted at a pressure within about 0.5 torr, 1 torr, 2 torr, 3 torr, 4 torr, 5 torr, 6 torr, 7 torr, 8 torr, 9 torr, 10 torr, 50 torr, or 100 torr of the plasma gas pressure. In other embodiments, the ionization step may be conducted at a pressure within about 0.1 torr to about 10.0 torr, about 0.5 torr to about 10.0 torr, about 1.0 torr to about 10.0 torr, about 0.1 torr to about 5.0 torr, about 0.5 torr to about 5.0 torr, about 1.0 torr to about 5.0 torr, about 0.1 torr to about 2.0 torr, about 0.5 torr to about 2.0 torr, about 1.0 torr to about 2.0 torr, about 0.1 torr to about 1.0 torr, or about 0.5 torr to about 1.0 torr of the plasma gas pressure.

Figure 2:
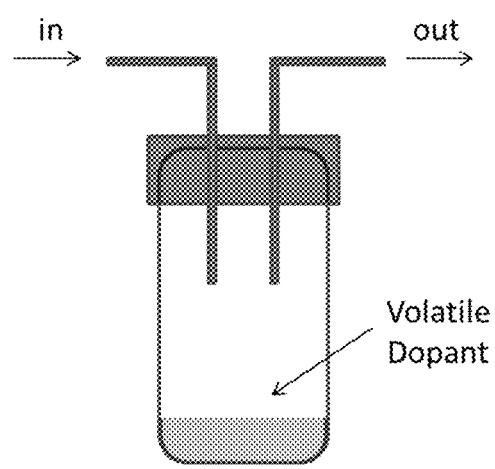
FIG. 2: Dopant gas mixtures were prepared by placing volatile liquid samples in a glass bottle as shown. Air or nitrogen with ~1 bar pressure was used as the carrier gas.

In an embodiment, dopant gasses may be prepared for introduction into the mass spectrometric system by placing a volatile liquid sample of the desired dopant compounds in a container, and then passing one or more carrier gasses through the container (FIG. 2). Carrier gasses transport the volatile dopant gasses into the system. The dopant is introduced downstream from the CRI plasma cavity, but before the sample is transported into the mass spectrometer.

In certain embodiments, the dopant molecules introduced downstream of the plasma reaction product stream is a low ionization potential dopant. In an embodiment, the ionization potential of the dopant molecule is less than that of the element for which analysis is being conducted. In another embodiment, the ionization potential of the dopant molecule is less than that of the carrier gas. In another embodiment, the ionization potential of the dopant molecule is less than the energy level of the metastable species of the carrier gas.

In an embodiment, the dopant has an ionization potential of less than 16.0 eV. In an embodiment, the dopant has an ionization potential of less than 15.0 eV. In an embodiment, the dopant has an ionization potential of less than 14.0 eV. In an embodiment, the dopant has an ionization potential of less than 13.0 eV. In another embodiment, the dopant has an ionization potential of less than 11.0 eV. In another embodiment, the dopant has an ionization potential of less than 12.0 eV. In another embodiment, the dopant has an ionization potential of about 6.0 eV to about 16.0 eV, 6.0 eV to about 15.0 eV, about 6.0 eV to about 14.0 eV., about 6.0 eV to about 13.0 eV, 6.0 eV to about 12.0 eV, or about 6.0 eV to about 11.0 eV. In another embodiment, the dopant has an ionization potential of about 6.0 eV to about 8.0 eV, about 8.0 eV to about 10.0 eV, about 10.0 eV to about 12.0 eV, about 12.0 eV to about 14.0 eV, or about 14.0 eV to about 16.0 eV.

In an embodiment, the dopant is selected from a common industrial gas. In another embodiment, the dopant may be one or more compounds selected from the group consisting of acetaldehyde, acetic acid, acetone, acetylene, acrolein, acrylonitrile, allene, allyl alcohol, allyl chloride, aminoethanol, 2-amino pyridine, ammonia, aniline, argon, arsine, atmospheric air, benzaldehyde, benzene, benzenethiol, benzoic acid, bromobenzene, bromobutane, bromobutane, bromobutanone, 1-bromo-2-chloroethane, bromoethane, bromoethene, bromoform, 1-bromo-3-hexanone, bromomethane, bromomethyl ethyl ether, 1-bromo-2-methylpropane, 2-bromo-2-methylpropane, bromopentane, 1-bromopropane, 2-bromopropane, 1-bromo-2-propene, 2-bromopropene, 3-bromopropene, 2-bromothiophene, o-bromotoluene, m-bromotoluene, p-bromotoluene, 1,3-butadiene, 2,3-butadione, n-butanal, s-butanal, n-butane, n-butanol, s-butanol, t-butanol, 2-butanone, 1-butene, cis-2-butene, 3-trans-2-butene, n-butyl acetate, s-butyl acetate, t-butyl acetate, n-butyl alcohol, n-butylamine, s-butylamine, t-butylamine, n-butylbenzene, t-butylbenzene, butyl cellosolve, n-butyl mercaptan, t-butyl mercaptan, p-tert-butyltoluene, 1-butyne, 2-butyne, n-butyraldehyde, carbon disulfide, carbon tetrachloride, chloroacetaldehyde, chlorobenzene, 1-chloro-2-bromoethane, 1-chlorobutane, 2-chlorobutane, 1-chlorobutanone, 1-chloro-2,3-epoxypropane, chloroethene, 2-chloroethoxyethene, 1-chloro-2-fluorobenzene, 1-chloro-3-fluorobenzene, cis-1-chloro-2-fluoroethene, trans-1-chloro-2-fluoroethene, chloroform, o-chloroiodobenzene, chloromethylethyl ether, chloromethylmethyl ether, 1-chloro-2-methylpropane, 1-chloropropane, 2-chloropropane, 3-chloropropene, 2-chlorothiophene, o-chlorotoluene, m-chlorotoluene, p-chlorotoluene, o-cresol, m-cresol, p-cresol, crotonaldehyde, cumene, cyanoethene, cyanogen bromide, 3-cyanopropene, cyclobutane, cyclohexane, cyclohexanol, cyclohexanone, cyclohexene, cyclo-octatetraene, cyclopentadiene, cyclopentane, cyclopentanone, cyclopentene, cyclopropane, 2-decanone, dibromochloromethane, 1,1-dibromoethane, dibromomethane, 1,2-dibromopropane, dibutylamine, 1,2-dichlorobenzene, 1,1-dichloroethane, 1,2-dichloroethane, 1,1-dichloroethene, cis-1,2-dichloroethene, trans-1,2-dichloroethene, dichloromethane, 1,2-dichloropropane, 1,3-dichloropropane, 1,1-dichloropropanone, 2,3-dichloropropene, dicyclopentadiene, diethoxymethane, diethylamine, diethylamino ethanol, diethyl ether, diethyl ketone, diethyl sulfide, 1,2-difluorobenzene, 1,4-difluorobenzene, difluoromethylbenzene, diiodomethane, diisobutyl ketone, diisopropylamine, 1,1-dimethoxyethane, dimethoxymethane, dymethylamine, dimethylaniline, 2,3-dimethylbutadiene, 2,2-dimethylbutane, 2,3-dimethylbutane, 2,2-dimethylbutan-3-one, 3,3-dimethylbutanone, 2,3-dimethyl-2-butene, dimethyl disulfide, dimethyl ether, 3,5-dimethyl-4-deptanone, 1,1-dimethylhydrazine, 2,2-dimethyl-3-pentanone, 2,2-dimethylpropane, dimethyl sulfide (DMS), di-n-propylamine, di-n-propyl disulfide, di-n-propyl ether, di-i-propyl ether, di-n-propyl sulfide, epichlorohydrin, ethane, ethanethiol (ethyl mercaptan), ethanol, ethanolamine, ethene (ethylene), ethyl acetate, ethylamine, ethyl amyl ketone, ethylbenzene, ethyl bromide, ethyl butyl ketone, ethyl chloroacetate, ethyl disulfide, ethyl ethanoate, ethyl ether, ethylene chlorohydrin, ethylene dibromide, ethylene oxide, ethyl formate, ethyl iodide, ethyl isothiocyanate, ethyl methanoate, ethyl methyl sulfide, ethyl propanoate, ethyl trichloroacetate, mono-fluorobenzene, mono-fluoroethene, mono-floromethanal, fluorotribromomethane, o-fluorotoluene, m-fluorotoluene, p-fluorotoluene, furan, furfural, helium, n-heptane, 2-heptanone, 4-heptanone, n-hexane, 2-hexanone, 1-hexene, hydrogen selenide, hydrogen sulfide, hydrogen telluride, iodobenzene, 1-iodobutane, 2-iodobutane, iodoethane (ethyl iodide), iodomethane (methyl iodide), 1-iodo-2-methylpropane, 1-iodopentane, 1-iodopropane, 2-iodopropane, o-iodotoluene, m-iodotoluene, p-iodotoluene, isoamyl acetate, isoamyl alcohol, isobutane, isobutanol, isobutyl acetate, isobutyl alcohol, isobutylamine, isobutylbenzene, isobutylene, isobutyl ethanoate, isobutyl formate, isobutyl mercaptan, isobutyl methanoate, isobutyraldehyde, isopentane, isoprene, isopropyl acetate, isopropyl alcohol, isopropylamine, isopropylbenzene, isopropyl ether, isovaleraldehyde, ketene, mesitylene, mesityl oxide, methyl acetate, methanol, methylamine, methyl bromide, 2-methyl-1,3-butadiene, 2-methylbutanal, 2-methylbutane, 2-methyl-1-butene, 3-methyl-1-butene, 3-methyl-2-butene, methyl n-butyl ketone, methyl butyrate, methyl chloroacetate, methylchloroform, methylcyclohexane, methylcyclohexanol, methylcyclohexanone, 4-methylcyclohexene, methylcyclopropane, methyl dichloroacetate, methyl ethanoate, methyl ethyl ketone, methyl ethyl sulfide, 2-methyl furan, methyl iodide, methyl isobutyl ketone, methyl isobutyrate, methyl isopropyl ketone, methyl mercaptan, methyl methacrylate, 2-methylpentane, 3-methylpentane, 2-methylpropanal, 2-methylpropane, 2-methyl-2-propanol, 2-methylpropene, methyl n-propyl ketone, methyl styrene, napthalene, nitric oxide, nitrobenzene, p-nitrochlorobenzene, nitrogen, 5-nonanone, 3-octanone, 4-octanone, oxygen, 1-octene, cis-1,3-pentadiene, trans-1,3-pentadiene, n-pentanal, n-pentane, 2,4-pentanedione, 2-pentanone, 3-pentanone, 1-pentene, perfluoro-1-heptene, n-perfluoropropyl Iodide, n-perfluoropropyl-iodomethane, n-perfluoropropyl-methyl ketone, phenol, phenyl ether, phenyl isocyanate, phosphine, pinene, propadiene, n-propanal, propane, 1-propanethiol (n-propyl mercaptan), n-propanol, propanone, propene, prop-1-ene-2-ol, prop-2-ene-1-ol, propionaldehyde, n-propyl acetate, n-propyl alcohol, n-propylamine, propylbenzene, propylene, propylene imine, propylene oxide, n-propyl ether, n-propyl formate, propane, pyridine, styrene, tetrachloroethylene (PCE), tetrafluoroethene, tetrahydrofuran, thioethanol, thiomethanol, thiophene, 1-thiopropanol, toluene, o-toluidine, tribromoethene, 1,1,1-trichlorobutanone, 1,1,1-trichloroethane, trichloroethylene (TCE), trichloromethyl ethyl ether, triethylamine, 1,2,4-trifluorobenzene, 1,3,5-trifluorobenzene, trifluoroethene, 1,1,1-trifluoro-2-iodoethane, trifluoroiodomethane, trifluoromethylbenzene, trifluoromethylcyclohexane, 1,1,1-trifluoropropene, trimethylamine, 2,2,4-trimethyl pentane, 2,2,4-trimethyl-3-pentanone, n-valeraldehyde, vinyl acetate, vinyl bromide, vinyl chloride, 4-vinylcyclohexene, vinyl ethanoate, vinyl fluoride, vinyl methyl ether, o-vinyl toluene, o-xylene, m-xylene, p-xylene, and 2,4-xylidine.

In certain embodiments, dopant contains one or more compound(s) or compositions selected from acetone, toluene, benzoic acid, nitrogen ($N_2$), oxygen ($O_2$), ammonia ($NH_3$), atmospheric air, water, and methanol.

Dopants with low ionization potentials may be chosen in order to produce negatively charged element-specific reaction products. The ability of the present invention to produce negatively charged element-specific products are of particular use for elements that have high ionization potentials, for example the halogens such as fluorine, chlorine, and bromine.

In certain embodiments the plasma is a helium plasma or argon plasma.

The foregoing methods, apparatuses, and kits provide for the quantitative analysis of a variety of analytes. In particular embodiments, the analytes may be non-volatile chemical compounds. In certain embodiments, the analyte is from a petrochemical analyte, an agrochemical analyte, a biological analyte, or a pharmaceutical analyte. In certain embodiments, the analyte is an organic chemical compound, including but not limited to an amino acid, a carbohydrate, a nucleic acid, a polypeptide, a protein, or a lipid.

In certain embodiments, the analyte comprises one or more atoms that have a first ionization potential of 9.0 eV or greater. In certain embodiments, the analyte comprises one or more atoms that have a first ionization potential of 10.0 eV or greater. In certain embodiments, the analyte comprises one or more atoms that have a first ionization potential of 11.0 eV or greater. In certain embodiments, the analyte comprises one or more atoms that have a first ionization potential of 12.0 eV or greater. In other embodiments, the analyte comprises one or more atoms that have a first ionization potential of 13.0 eV or greater. In other embodiments, the analyte comprises one or more atoms that have a first ionization potential of 14.0 eV or greater. In other embodiments, the analyte comprises one or more atoms that have a first ionization potential of 15.0 eV or greater. In other embodiments, the analyte comprises one or more atoms that have a first ionization potential of 16.0 eV or greater. In other embodiments, the analyte comprises one or more atoms that have a first ionization potential of 17.0 eV or greater.

In certain embodiments, the analyte of the present invention comprises one or more halogen atoms. In particular embodiments, the halogen atom is selected from one or more halogen atoms from the group consisting of fluorine, bromine, and chlorine. In specific embodiments, the analyte contains fluorine.

In certain embodiments, the analyte contains nitrogen, oxygen, and/or sulfur.

In an embodiment of the present invention, PARCI may be utilized for breaking down organohalogens to simple halogen-containing molecules (e.g. HBr, HCl, HF) in a helium or argon plasma followed by negative mode chemical ionization (CI) in the afterglow region. The reagent ions for CI originate from penning ionization of gases (e.g. $N_2$, $O_2$, Ar) introduced into the afterglow region.

The performance of PARCI-mass spectrometry (MS) has been evaluated using flow injection analyses of for example, organobromines, demonstrating 5-8 times better sensitivities compared to inductively coupled plasma MS.

Definitions

All definitions, as defined and used herein, should be understood to control over dictionary definitions, definitions in documents incorporated by reference, and/or ordinary meanings of the defined terms.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "about," as used herein in reference to quantitative measurements, refers to the indicated value plus or minus 10%.

As used herein, "biological sample" refers to any sample from a biological source.

Chromatography

As used herein, "chromatography" refers to a process in which a chemical mixture carried by a liquid or gas is separated into components as a result of differential distribution of the chemical entities as they flow around or over a stationary liquid or solid phase.

As used herein, "gas chromatography" means a process in which the mixture of components may be separated, when such a mixture diffused along with a carrier gas through a liquid or solid adsorbent for differential adsorption. Differential adsorption of the components with the adsorbent allows for separation of the constituent components.

As used herein, "liquid chromatography" (LC) means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes reverse phase liquid chromatography (RPLC), high performance liquid chromatography (HPLC) and high turbulence liquid chromatography (HTLC).

As used herein, the term "HPLC" or "high performance liquid chromatography" refers to liquid chromatography in which the degree of separation is increased by forcing the mobile phase under pressure through a stationary phase, typically a densely packed column.

As used herein, the term "gas chromatography" refers to chromatography in which the sample mixture is vaporized and injected into a stream of carrier gas (e.g., nitrogen, argon, or helium) moving through a column containing a stationary phase composed of a liquid or a particulate solid and is separated into its component compounds according to the affinity of the compounds for the stationary phase.

Mass Spectrometry

As used herein, "mass spectrometry" (MS) refers to an analytical technique to identify compounds by their mass. MS technology generally includes (1) ionizing the compounds to form charged compounds; and (2) detecting the molecular weight of the charged compound and calculating a mass-to-charge ratio (m/z). The compound may be ionized and detected by any suitable means. A "mass spectrometer" generally includes an ionizer and an ion detector.

The term "electron ionization" and "electron impact" as used herein refers to methods in which an analyte of interest in a gaseous or vapor phase interacts with a flow of electrons. Impact of the electrons with the analyte produces analyte ions, which may then be subjected to a mass spectrometry technique.

The term "fast atom bombardment" as used herein refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine.

The term "field desorption" as used herein refers to methods in which a non-volatile test sample is placed on an ionization surface, and an intense electric field is used to generate analyte ions.

The term "ionization" as used herein refers to the process of generating an analyte ion having a net electrical charge equal to one or more electron units. Negative ions are those having a net negative charge of one or more electron units, while positive ions are those having a net positive charge of one or more electron units.

The term "operating in negative ion mode" refers to those mass spectrometry methods where negative ions are detected. Similarly, "operating in positive ion mode" refers to those mass spectrometry methods where positive ions are detected.

The term "desorption" as used herein refers to the removal of an analyte from a surface and/or the entry of an analyte into a gaseous phase.

The term "chemical ionization" as used herein refers to methods in which a reagent gas (e.g., ammonia) is subjected to electron impact, and analyte ions are formed by the interaction of reagent gas ions and analyte molecules.

Test Samples

Suitable test samples include any test sample that may contain one or more analyte(s) of interest. For example, samples obtained during the manufacture of an analyte can be analyzed to determine the composition and yield of the manufacturing process. In some embodiments, a sample is a biological sample; that is, a sample obtained from any biological source, such as an animal, a cell culture, an organ culture, etc. In certain embodiments, samples are obtained from a mammalian animal, such as a dog, cat, horse, etc. Exemplary mammalian animals are primates, most preferably humans. Exemplary samples include blood, plasma, serum, hair, muscle, urine, saliva, tear, cerebrospinal fluid, or other tissue sample. Such samples may be obtained, for example, from a patient; that is, a living person presenting oneself in a clinical setting for diagnosis, prognosis, or treatment of a disease or condition. The test sample may be obtained from a patient, for example, blood serum.

Sample Preparation for Mass Spectrometry

Samples may be processed or purified to obtain preparations that are suitable for analysis by mass spectrometry. Such purification will usually include chromatography, such as liquid chromatography, and may also often involve an additional purification procedure that is performed prior to chromatography.

Various procedures may be used for this purpose depending on the type of sample or the type of chromatography. Examples include filtration, extraction, precipitation, centrifugation, delipidization, dilution, combinations thereof and the like. Protein precipitation is one method of preparing a liquid biological sample, such as serum or plasma, for chromatography. Such protein prescription methods are well known in the art, for example, Polson et al., *Journal of Chromatography B* 785:263-275 (2003), describes protein precipitation methods suitable for use in the methods of the invention.

Samples can be centrifuged to separate the liquid supernatant from the precipitated proteins. The resultant supernatant can then be applied to liquid chromatography and subsequent mass spectrometry analysis. In one embodiment of the invention, the protein precipitation involves adding one volume of the liquid sample (e.g., plasma) to about four volumes of methanol. In another embodiment, the protein precipitation involves adding two volumes of liquid sample (e.g., plasma) to about three volumes of methanol. In certain embodiments of protein precipitation, the methanol solution contains an internal standard and/or the adduct. In certain embodiments, the use of protein precipitation obviates the need for high turbulence liquid chromatography ("HTLC") or on-line extraction prior to HPLC and mass spectrometry. Accordingly in such embodiments, the method involves (1) performing a protein precipitation of the sample of interest; and (2) loading the supernatant directly onto the HPLC-mass spectrometer without using on-line extraction or high turbulence liquid chromatography ("HTLC").

Liquid Chromatography

Generally, chromatography may be performed prior to mass spectrometry; the chromatography may be liquid chromatography, such as high performance liquid chromatography (HPLC).

Liquid chromatography (LC) including high-performance liquid chromatography (HPLC) relies on relatively slow, laminar flow technology. Traditional HPLC analysis relies on column packing in which laminar flow of the sample through the column is the basis for separation of the analyte of interest from the sample. One of ordinary skill in the art will understand that separation in such columns is a diffusional process. HPLC has been successfully applied to the separation of compounds in biological samples.

One of ordinary skill in the art can select HPLC instruments and columns that are suitable for use in the invention. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties.

One suitable bonded surface is a hydrophobic bonded surface such as an alkyl bonded surface. Alkyl bonded surfaces may include C-4, C-8, or C-18 bonded alkyl groups, preferably C-18 bonded groups.

The chromatographic column includes an inlet port for receiving a sample and an outlet port for discharging an effluent that includes the fractionated sample. In one embodiment, the sample (or pre-purified sample) is applied to the column at the inlet port, eluted with a solvent or solvent mixture, and discharged at the outlet port. Different solvent modes may be selected for eluting the analytes of interest. For example, liquid chromatography may be performed using a gradient mode, an isocratic mode, or a polytypic (i.e., mixed) mode. During chromatography, the separation of materials is effected by variables such as choice of eluent (also known as a "mobile phase"), choice of gradient elution and the gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

Recently, high turbulence liquid chromatography ("HTLC"), also called high throughput liquid chromatography, has been applied for sample preparation prior to analysis by mass spectrometry. (See, e.g., Zimmer et al., *J. Chromatogr. A* 854:23-35 (1999); see also, U.S. Pat. Nos. 5,968,367; 5,919,368; 5,795,469; and 5,772,874). Traditional HPLC analysis relies on column packing in which laminar flow of the sample through the column is the basis for separation of the analyte of interest from the sample. The skilled artisan will understand that separation in such columns is a diffusional process. In contrast, it is believed that turbulent flow, such as that provided by HTLC columns and methods, may enhance the rate of mass transfer, improving the separation characteristics provided.

Mass spectrometry may be performed using a mass spectrometer which includes an ion source for ionizing the fractionated sample and creating charged molecules for further analysis.

As described in the foregoing description of the invention, ionization of the elemental reaction products may be accomplished by interaction with the charged ionization products. The charged ionization products result from ionization of dopant molecules introduced downstream from the plasma CRI.

In certain embodiments of the present invention, there may be additional sources of ionization. For example ionization of the sample may be performed by electrospray ionization (ESI), atmospheric pressure chemical ionization (APCI), atmospheric pressure photoionization (APPI), photoionization, penning ionization, electron ionization, fast atom bombardment (FAB)/liquid secondary ionization (LSIMS), matrix assisted laser desorption ionization (MALDI), field ionization, field desorption, thermospray/plasmaspray ionization, and particle beam ionization. One of ordinary skill in the art will understand that the choice of ionization method can be determined based on the analyte to be measured, type of sample, the type of detector, the choice of positive versus negative mode, etc.

After an elemental reaction product has been ionized, the positively charged or negatively charged ions thereby created may be analyzed to determine a mass-to-charge ratio (i.e., m/z). Suitable analyzers for determining mass-to-charge ratios include quadrupole analyzers, ion traps analyzers, and time-of-flight analyzers. The ions may be detected using several detection modes. For example, selected ions may be detected (i.e., using a selective ion monitoring mode (SIM)), or alternatively, ions may be detected using a scanning mode, e.g., multiple reaction monitoring (MRM) or selected reaction monitoring (SRM). In an embodiment, the mass-to-charge ratio can determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

One may enhance the specificity of the MS technique by employing "tandem mass spectrometry," or "MS/MS." In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collision with atoms of an inert gas to produce the daughter ions. Because both the precursor and fragment ions are produced in a reproducible fashion under a given set of ionization/fragmentation conditions, the MS/MS technique can provide an extremely powerful analytical tool. For example, the combination of filtration fragmentation can be used to eliminate interfering substances, and can be particularly useful in complex samples, such as biological samples.

The mass spectrometer typically provides the user with an ion scan; that is, the relative abundance of each ion with a particular m/z over a given range (e.g., 100 to 2000 amu). The results of an analyte assay, that is, a mass spectrum, can be related to the amount of the analyte in the original sample by numerous methods known in the art. For example, given that sampling and analysis parameters are carefully controlled, the relative abundance of a given ion can be compared to a table that converts that relative abundance to an absolute amount of the original molecule. Alternatively, molecular standards can be run with the samples, and a standard curve constructed based on ions generated from those standards. Using such a standard curve, the relative abundance of a given ion can be converted into an absolute amount of the original molecule.

One or more steps of the methods of the invention can be performed using automated machines. In certain embodiments, one or more purification steps are performed on line, and more preferably all of the purification and mass spectrometry steps may be performed in an on-line fashion.

In certain embodiments, such as MS/MS, where precursor ions are isolated for further fragmentation, collisionally activated dissociation (CAD) is often used to generate the fragment ions for further detection. In CAD, precursor ions gain energy through collisions with an inert gas, and subsequently fragment by a process referred to as "unimolecular decomposition". Sufficient energy must be deposited in the precursor ion so that certain bonds within the ion can be broken due to increased vibrational energy.

EXAMPLES

The following examples describe the coupling of a plasma cavity to a mass spectrometer (MS). Additionally, the example below illustrates ionization of dopant molecules using metastable species from microwave induced plasma.

Example 1: Plasma Generation and System Setups

A. PARCI System with Nitrogen Gas Carrier

A setup for microwave induced plasma was assembled. Experiments were conducted with a microwave cavity assembled based on Bowman design (see *Biol. Mass Spectrum.* 21, 693-699 (1992)), and plasmas were formed at 1-50 Torr in helium or mixture of helium with air, or nitrogen.

A schematic of the experimental setup is shown in FIG. 1. Microwave induced plasma was generated in a ceramic tube with 0.25" OD inserted in the home-made microwave cavity. A momentum separator was used to reduce the pressure from atmosphere to the pressure of the plasma. As shown in FIG. 1, carrier gas (with analytes) can be introduced upstream of the momentum separator, plasma gas (including reactant gas) can be introduced after the momentum separator but before the microwave cavity, and the dopant or ionization gas can be introduced downstream right before the entrance of the mass spectrometer.

To couple the plasma cavity to the MS, the source block of a Flexar SQ300 MS (PerkinElmer) was completely removed. The glass inlet capillary was replaced with a stainless steel tube of 0.25" OD and 0.084" ID. This allowed operation of the plasma at 1-50 Torr with sufficient flow into the MS to maximize ion transfer. The pressure is monitored by a diaphragm vacuum gauge installed on the momentum separator upstream of the plasma.

The plasma gas flow can be controlled by needle valves. The nitrogen carrier gas flow sampled by the momentum separator was 1.5 L/min, when the plasma pressure reached 20 torr. The plasma of helium can be self-ignited or ignited by Tesla coil.

Ionization reagents were created via reaction of metastable species from plasma with dopants or ionization gas introduced downstream of the plasma. Dopants with low ionization potential supply the electrons for ionization of species formed in the plasma. Dopant gas mixtures were prepared by placing volatile liquid samples in a glass bottle as shown in FIG. 2. Air or nitrogen with ~1 bar pressure was used as the carrier gas for dopants.

B. PARCI System with Helium Gas Carrier and Liquid Sample Introduction

Figure 6:
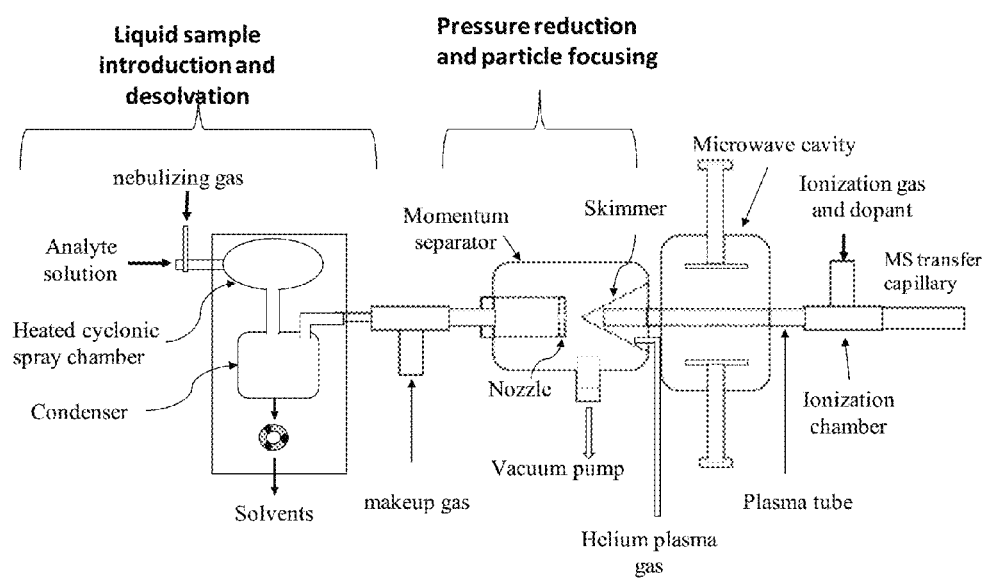
FIG. 6: A schematic diagram of a PARCI apparatus for Chemical Reaction Interface Mass Spectrometry with liquid solution sample introduction comprising means for spraying the solution at atmospheric pressure, desolvation of the spray, pressure reduction and particle focusing into a chemical reaction interface (CRI) plasma cavity, and introducing a dopant molecule and/or ionization gas downstream of the CRI plasma cavity.

A second experimental setup, similar to the PARCI system described in Section I supra, was assembled with helium carrier gas instead of nitrogen and liquid solution sample introduction. (FIG. 6)

Solutions containing analytes in 5:95 acetonitrile:water are introduced by flow injection at 50 μL/min using an HPLC pump (Series 200, PerkinElmer Inc., Shelton, Conn.) and a manual injection valve (FLOM Injector VI, Perkin Elmer Inc., Shelton, Conn.) with a 20 μL loop. Analyte solution is sprayed at atmospheric pressure into a desolvation unit (APEX E, Elemental Scientific Inc., Omaha, Nebr.) using a high efficiency nebulizer (HEN-90-A0.1, Meinhard Glass Products, Golden, Colo.). The nebulizer gas flow is controlled by a mass flow controller (Type M100B, MKS Instruments Inc., Andover, Mass.).

C. Sample Introduction System

Within the APEX desolvation unit, the aerosols pass through a heated cyclonic spray chamber followed by a cooled condenser, resulting in reduction of solvent load into the plasma. This reduction is necessary to prevent excessive cooling of the low-pressure plasma. A makeup gas is added after the desolvation step if helium gas is used for nebulization. This configuration allows operation of desolvation at optimum gas flow rate while maintaining the total flow sampled by the ion source.

For transition from atmospheric pressure to the plasma pressure, a homemade momentum separator is used. The momentum separator consists of a stainless steel plate with 0.4 mm orifice (Lenox Lasers Inc., Glenn Arm, Md.) and a 0.88 mm skimmer (NEXION skimmer, PerkinElmer Inc., Shelton, Conn.) sealed in a 1"-i.d. brass housing. The orifice plate is mounted on a threaded tube, and the distance between the orifice and the skimmer is adjusted to ~2.5 mm. The brass housing is pumped by a mechanical pump (E2M28, Edwards Vacuum Inc., Sanborn, N.Y.) to ~7 Torr. The pressure was monitored by a capacitive monometer (Terranova Type 808, Duniway Stockroom Corp., Mountain View, Calif.) mounted on the brass housing. Desolvated aerosols from the APEX enter the momentum separator through the orifice. A majority of the aerosol carrier gas including the remaining solvent vapor is pumped away while the analytes within heavier particles are directed into the plasma. A total gas flow of ~4 L/min (for helium), dictated by the orifice size, is measured at the entrance of the momentum separator. A helium nebulizer gas flow of 600 mL/min and a helium makeup gas of ~3.4 L/min are used for analyses to provide the minimum flow and avoid pressure drop in the APEX unit.

Example 2: Ionization of Dopant Molecules

Preliminary experiments show the ionization of dopant molecules and detection of corresponding ions by the MS. Acetone, toluene, and benzoic acid were used as dopant molecules. Both positive and negative ions could be detected in their respective modes on the MS. The results for acetone (IP=9.7 eV) as the dopant molecule are discussed below.

Figure 3:
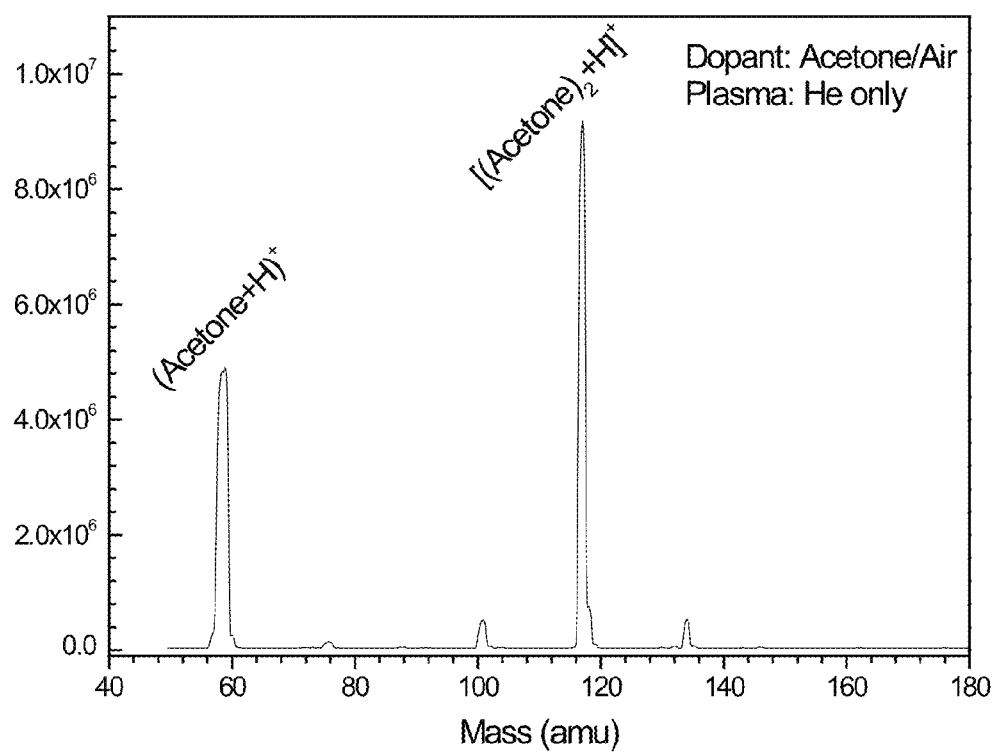
FIG. 3: The positive mode mass spectrum for acetone dopant with helium plasma at ~10 torr pressure. Two major peaks are identified as protonated acetone monomer and dimer.

FIG. 3 shows the positive mode mass spectrum for acetone with helium plasma at ~10 torr pressure using experimental setup of FIGS. 1 and 2. Two major peaks are identified as protonated acetone monomer and dimer.

Figure 4:
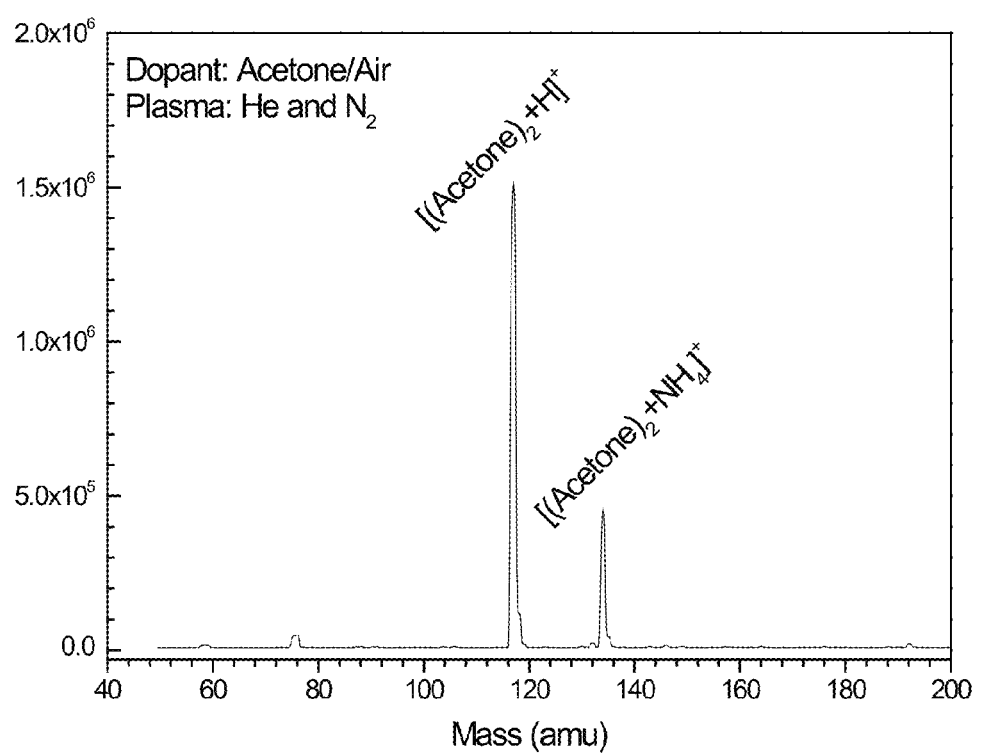
FIG. 4: The negative mode mass spectrum for acetone/air dopant with helium plasma at ~10 torr pressure. Note that laboratory air is used for dopant introduction, leading to appearance of nitrate anions.

Upon addition of ~1 torr nitrogen reaction gas into the plasma, the total ion current decreased. A mass spectrum collected under this condition is shown in FIG. 4. Protonated acetone intensity drops significantly. Formation of ammonium adduct also suggests ammonia formation within the plasma upon introduction of nitrogen. Note that ammonia has a higher proton affinity compared to acetone monomer and can neutralize protonated acetone. Also ammonium ion cannot be detected by SQ300 due to its low mass. Therefore, a drop in total ion current could be related to transfer of charge to low mass ions and subsequent elimination in the MS.

Figure 5:
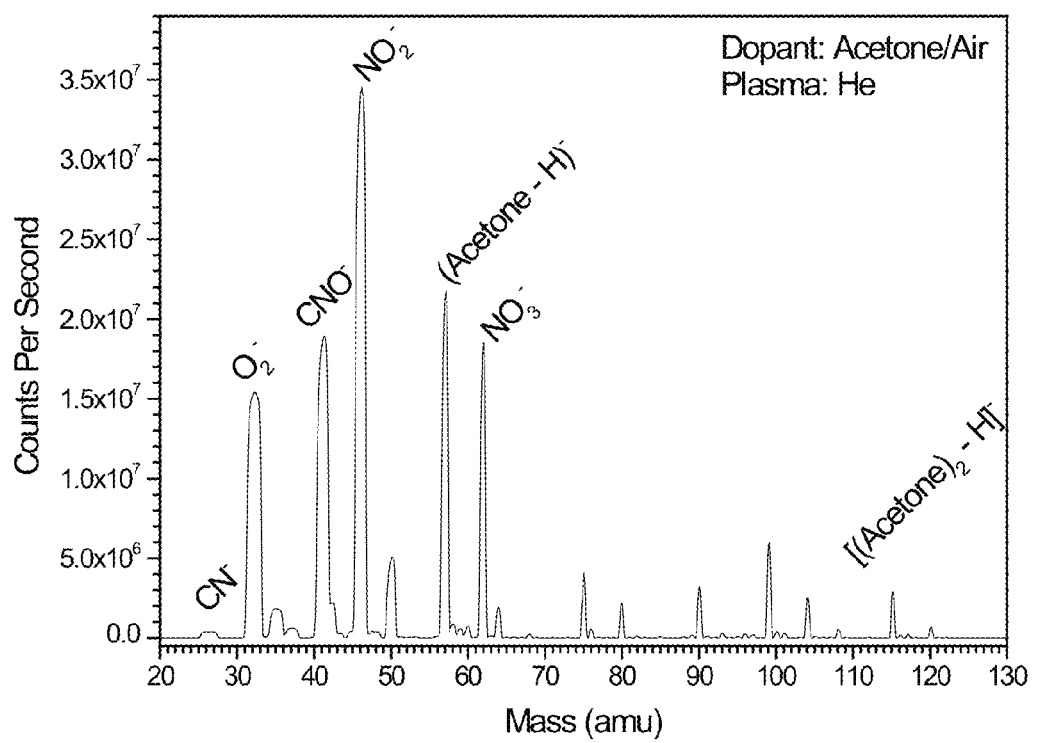
FIG. 5: The negative mode mass spectrum using air as ionization gas with helium plasma.

FIG. 5 shows the negative mode mass spectrum using experimental setup of FIGS. 1 and 2 for acetone dopant and helium plasma at ~10 torr pressure. Both deprotonated acetone monomer and dimer can be observed in the spectrum. Other relative stable anions, like $O_2^-$, $NO_2^-$ and $NO_3^-$ were also observed in the experiment.

Example 3: Mass Spectrum of Analytes Containing Halogen Elements

Solution samples were introduced with a nebulizer, and nitrogen as the nebulizing gas (FIG. 6). The nebulizer was coupled to a standard sample introduction system (Apex E, Elemental Scientific Inc.) comprised of a heated spray chamber and a peltier cooled condenser. Particles from outlet of the sample introduction system were swept into the momentum separator where they were sampled into the helium plasma. The plasma was first generated with helium injected downstream of the momentum separator. Pure oxygen was used as ionization gas. After the plasma was stabilized, gas flow of helium and oxygen were optimized for best signal/noise ratio in the mass spectra. Residual water in the carrier gas serves as reactant gas in this case. Therefore, no additional reactant gas is introduced into the plasma.

Figure 7:
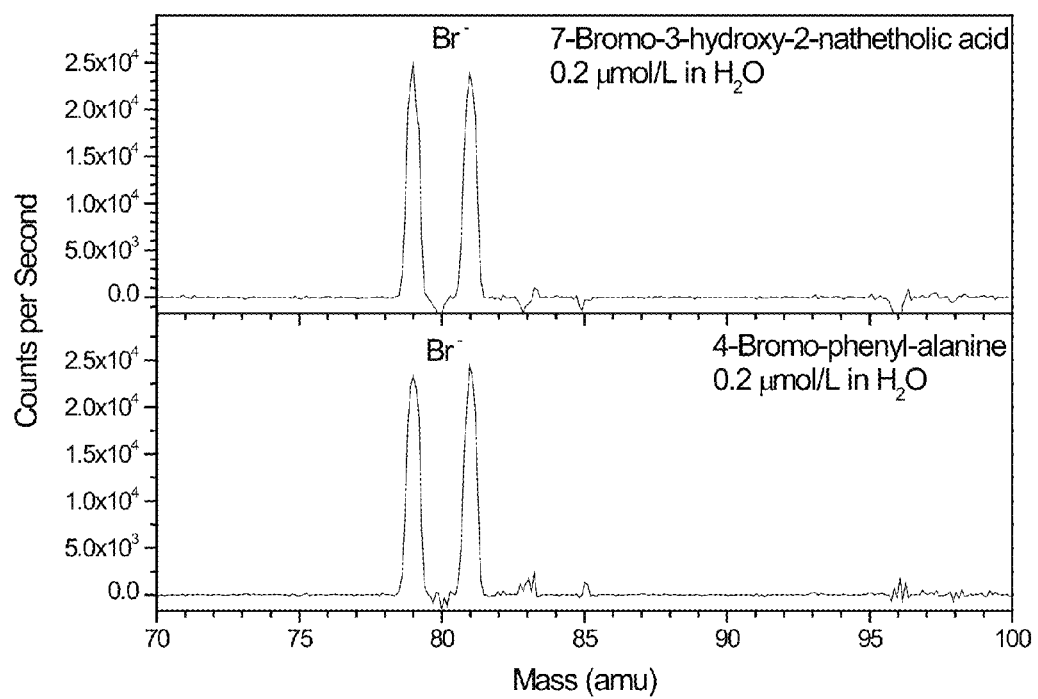
FIG. 7: Background subtracted negative mode mass spectrum of 7-bromo-3-hydroxy-2-naphthoic acid (top) and 4-bromo-phenyl-alanine (bottom) using oxygen as ionization gas nitrogen as nebulizer and makeup gas, and with helium plasma. Each sample was prepared with a concentration of 0.2 μM in water, with a 100 μL/min solution flow rate.

Mass spectra were first collected with only solvent (HPLC grade water) introduced, and these spectra were used as background spectra. FIG. 7 shows the background-subtracted spectra of two bromo-compounds, i.e. 7-bromo-3-hydroxy-2-naphthoic acid (top) 4-bromo-phenyl-alanine (bottom) in water (0.2 μM at a 100 μL/min solution flow rate). Two dominant peaks observed in the spectra represent two isotopes of bromine anion (mass=79 and 81).

Since the concentrations of both bromo-compounds are the same (0.2 μmol/L), the ion counts of Br⁻ anion are expected to be the same.

As shown in FIG. 7, the heights of peaks in both mass spectra are indeed the same. This example shows that the ion counts are independent of the structure of the analytes, and only depend on the concentration of the specific element.

The foregoing examples show that a microwave induced plasma chamber has been configured along with a plasma-MS interface. Ionization downstream of the plasma is demonstrated using dopant molecules and ionization gas. Both positive and negative ions were detected. When analytes introduced, the ion intensity only depends on the concentration of specific elements, and thus this technique can be used for quantitatively analysis of certain elements.

Figure 8:
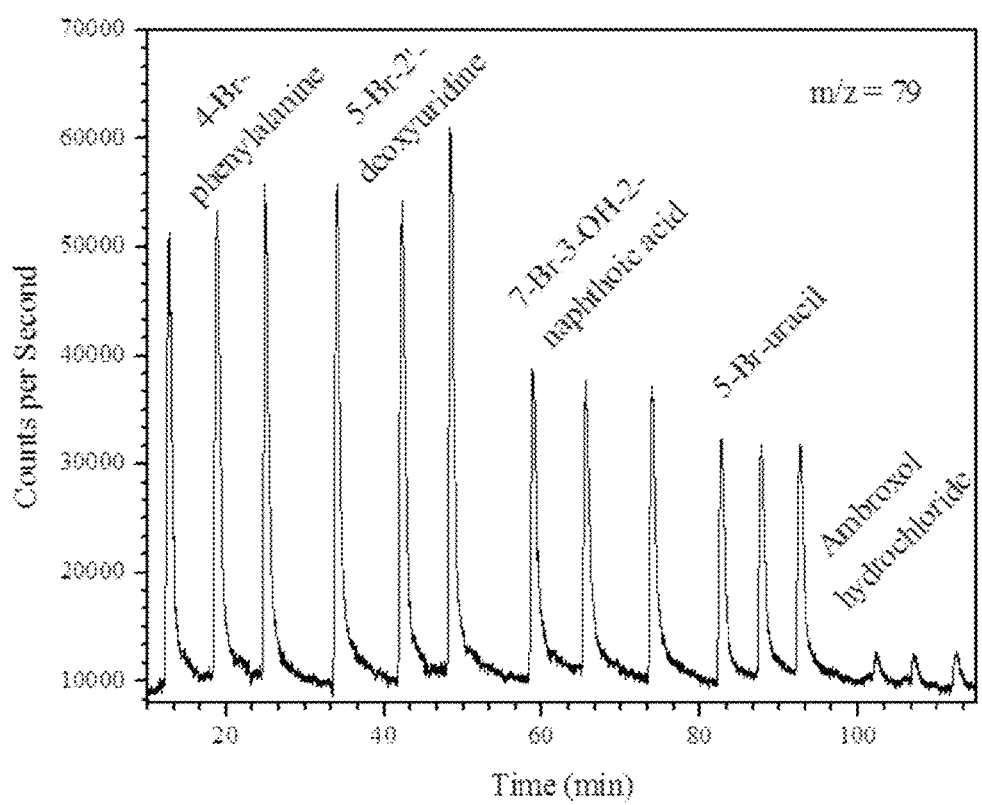
FIG. 8: Triplicate FIA (flow injection analysis) of brominated compounds using PARCI-MS using helium as nebulizer gas, makeup gas, and plasma gas and nitrogen as ionization gas.

Example 4: Comparison of PARCI-MS and ICP-MS Using Flow Injection PARCI-MS for Elemental Analysis of Brominated Compounds The performance of PARCI-MS was demonstrated through bromine detection by flow injection analyses (FIA) of six brominated organic compounds (FIG. 8) using the experimental setup of FIG. 6 with helium as nebulizer and makeup gas. For comparison with the current state-of-the-art method, FIA experiments of these compounds were also carried out on an ICP-MS instrument (7700x, Agilent).

FIA was used to mimic the coupling of PARCI-MS with liquid chromatography (LC). Nitrogen was utilized as ionization gas. Br⁻ ions were observed upon introduction of brominated compounds. Without being bound by theory, and in accordance with other reaction-based elemental methods (Hitzfeld, K. L., Gehre, M., Richnow, H. H., *Rapid Commun. Mass Spectrom.* 25(20), 3114-3122 (2011); Morre, J. T., Moini, *Biol. Mass Spectrom.* 21(12), 693-699 (1992)), it is proposed that bromide ions are formed from HBr generated within the high-temperature plasma via the reaction of brominated compounds with the residual solvent. Ionization of HBr can then proceed via electron capture within the ionization chamber as well as electron and proton transfer reactions with the reagent ions downstream of the ionization chamber.

To compare the performance of PARCI with ICP, FIA experiments were carried out on a commercial ICP-MS instrument (7700x, Agilent Technologies, Santa Clara, Calif.). In both methods, the mass spectrometer was operated with a dwell time of 0.5 s for each measured isotope. The ICP was operated with the RF power of 1500 W, nebulizer gas (argon) flow of 1.25 L/min, auxiliary gas flow of 0.9 L/min, outer gas flow of 15 L/min and sampling depth of 8.0 mm. FIA results for the six brominated compounds were obtained with the APEX desolvation unit using a micromist nebulizer (AR-30-1-FM005, Glass Expansion Inc., Pocasset, Mass.) at a solvent flow rate of 50 µL/min.

Figure 9:
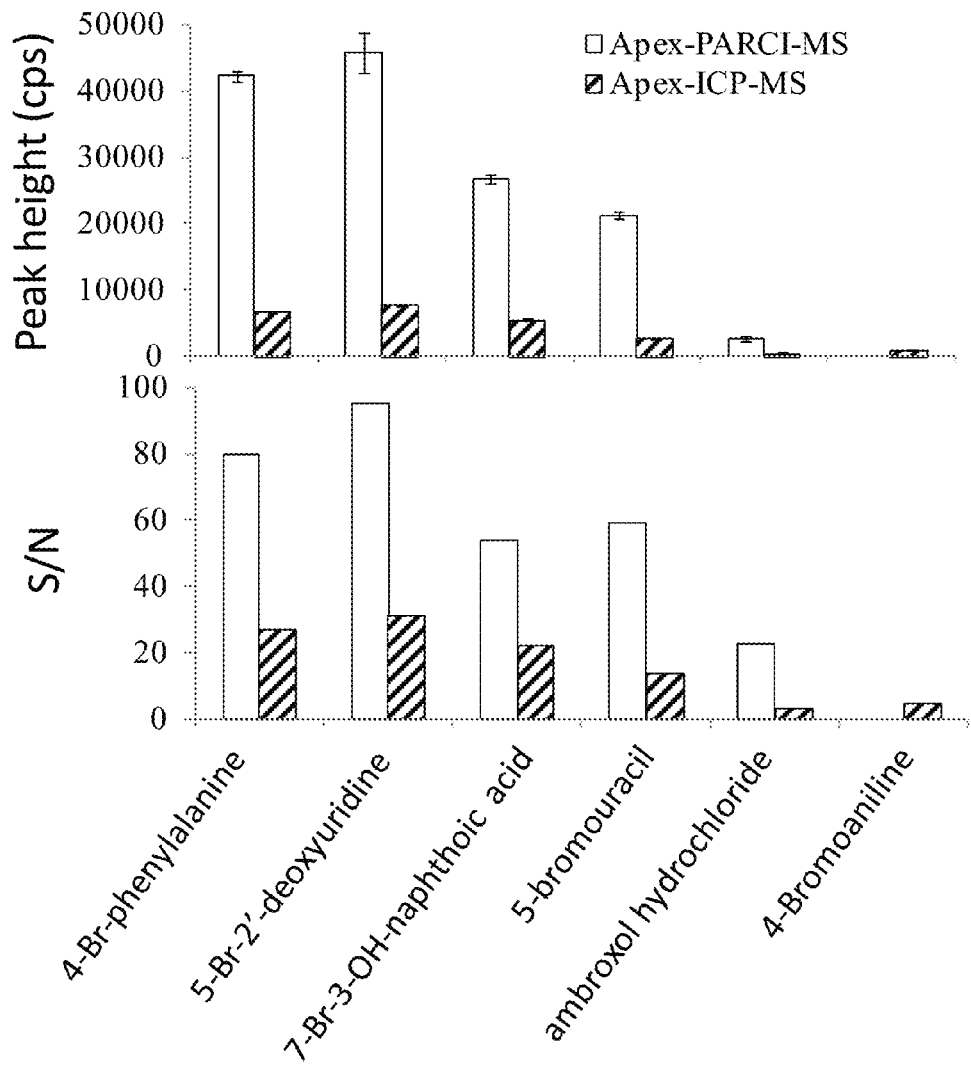
FIG. 9: Triplicate FIA (flow injection analysis) of brominated compounds comparing PARCI-MS and ICP-MS and signal to noise ratio of triplicate FIA (flow injection analysis) of brominated compounds comparing PARCI-MS and ICP-MS. An Apex system is used for nebulization and desolvation. PARCI-MS is operated with helium nebulizer gas, makeup gas, and plasma gas and nitrogen as ionization gas. ICP-MS is operated conventionally with argon as nebulizer and plasma gas.

FIG. 9 compares the performance of PARCI-MS to that of ICP-MS with an APEX desolvation unit coupled to PARCI-MS and ICP-MS. Both $^{79}$Br and $^{81}$Br isotopes are monitored while $^{79}$Br is used for sensitivity analysis in FIG. 9.

Note that the commercial ICP-MS is limited to positive ions while PARCI-MS is operated in negative mode for best performance. PARCI-MS shows 5-8 times higher flow injection peak heights and 3-8 times higher signal-to-noise ratios compared to ICP-MS for the first five compounds. Importantly, the better sensitivity of PARCI compared to ICP is despite the losses associated with particle focusing within the momentum separator and ion losses at the nozzle-skimmer region due to the large i.d. of the transfer tube.

High volatility of 4-bromoaniline leads to analyte loss within the desolvation unit and momentum separator, resulting in significantly lower sensitivities with PARCI-MS compared to ICP-MS. These observations imply that PARCI has the potential to produce superior performance in the absence of sample introduction biases.

The better performance of PARCI compared to other techniques can be attributed to efficient chemical ionization in negative mode and improved ion transmission due to lower space charge effects. A major advantage of PARCI is its facile coupling to atmospheric-sampling mass spectrometers. Accordingly, PARCI can be used to perform elemental and isotopic analysis on LC-MS instruments, providing a complimentary characterization method to other ion sources.

Figure 10:
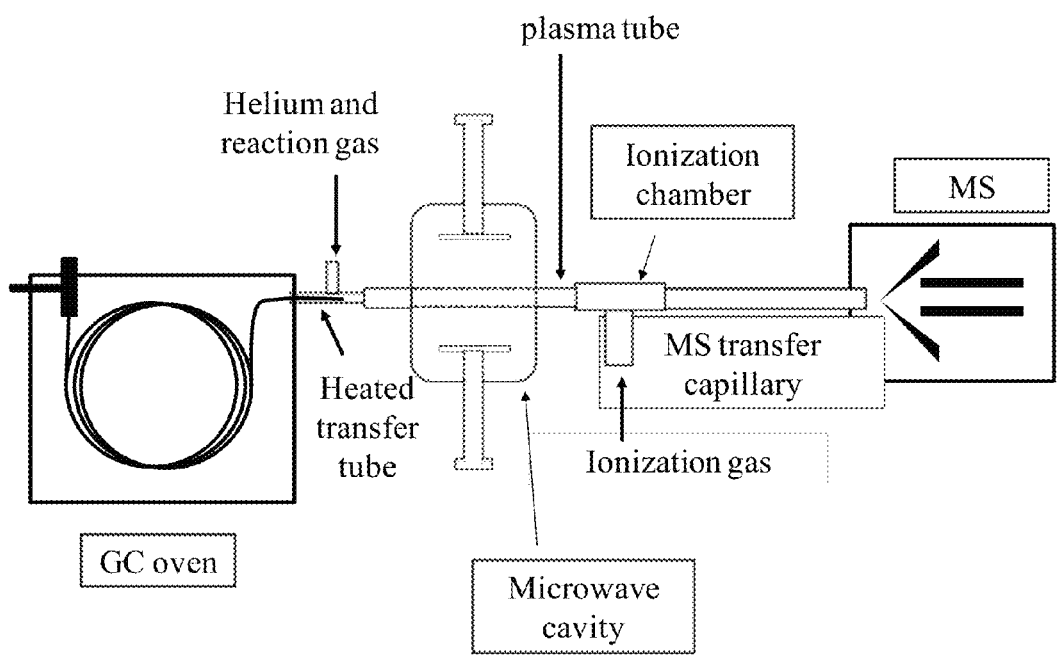
FIG. 10: A schematic diagram of a PARCI apparatus for Chemical Reaction Interface Mass Spectrometry with sample introduction comprising a gas chromatograph and means for introducing an ionization gas downstream of the Chemical Reaction Interface (CRI) plasma cavity.

Example 5: Gas Chromatography (GC) PARCI-MS for Elemental Analysis of Brominated Compounds A. Instrumentation A schematic drawing of the plasma-assisted reaction chemical ionization source combined with gas chromatography is presented in FIG. 10. Briefly, the setup consists of a sample introduction system, a plasma cavity, and an ionization chamber.

A gas chromatograph (GC) is used for the sample introduction. High purity helium is used as carrier gas for the GC, and the gas flow through the column is ~1.7 mL/min. The GC injector is operated with a split ratio of ~50. The outlet of the GC column is coupled to a ceramic tube inserted into the plasma cavity using a transfer line heated to ~200° C. A plasma gas is introduced at the gas inlet immediately before the ceramic tube to allow optimization of GC conditions while maintaining constant gas flow into the plasma. A reactant gas may be mixed with the plasma gas when necessary to promote reaction inside the plasma.

In current setup, a microwave cavity is utilized to generate plasma inside the ceramic tube. The plasma power is ~50 W. High purity helium is used as the plasma gas at the flow of ~45 mL/min. Water vapor is used as the reactant gas. The reactant gas is mixed into the plasma gas at a volume concentration of ~0.03%. GC eluent, plasma gas, and reactant gas interact with each other inside the plasma, generating element specific small molecules. These molecules are ionized inside the ionization chamber by chemical ionization, and the resultant ions are identified by mass spectrometry.

B. Results

Figure 11:
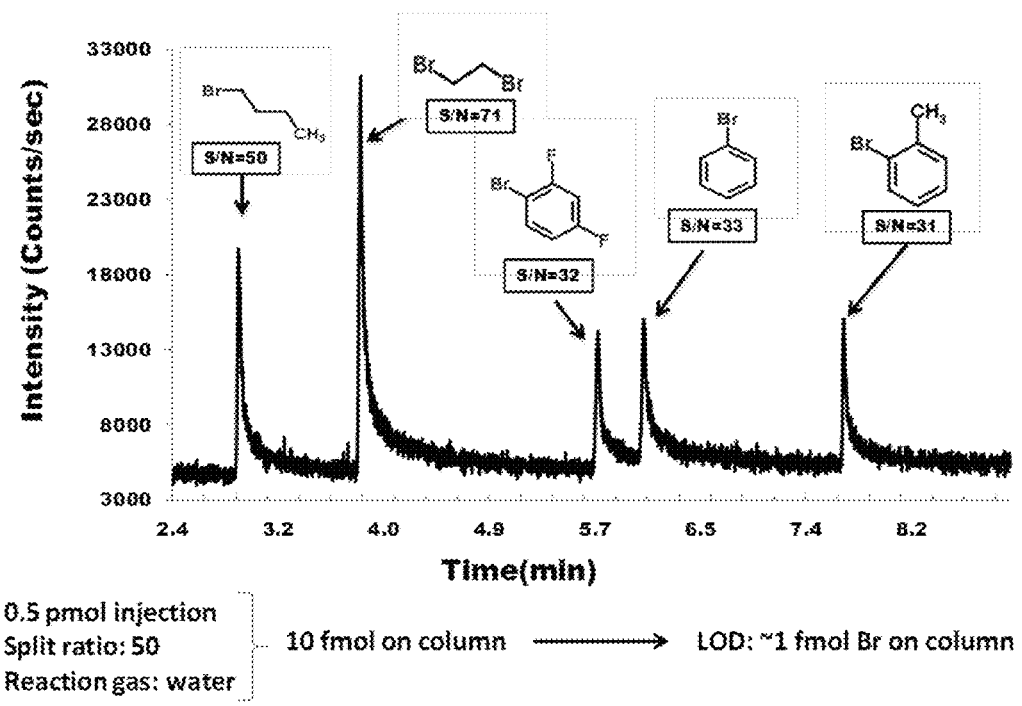
FIG. 11: GC-PARCI-MS of brominated compounds including signal to noise ratio. PARCI-MS is operated with helium-water mixture as reactant plasma gas, nitrogen as ionization gas. GC is operated with helium as carrier gas.

Mixed solution of five brominated compounds, 1-bromobutane, 1,2-dibromoethane, 1-bromo-2,4-difluorobenzene, bromobenzene, and bromotoluene were prepared in methanol. FIG. 11 presents the chromatograph corresponding to 0.5 pmol injection of the brominated compounds. Since the GC injector is operated at a split ratio of ~50, the actual bromine entered the PARCI is 10 fmol. As a result, the limit of detection is estimated to be ~1 fmol. GC-PARCI shows high sensitivity in bromine detection.

Figure 12:
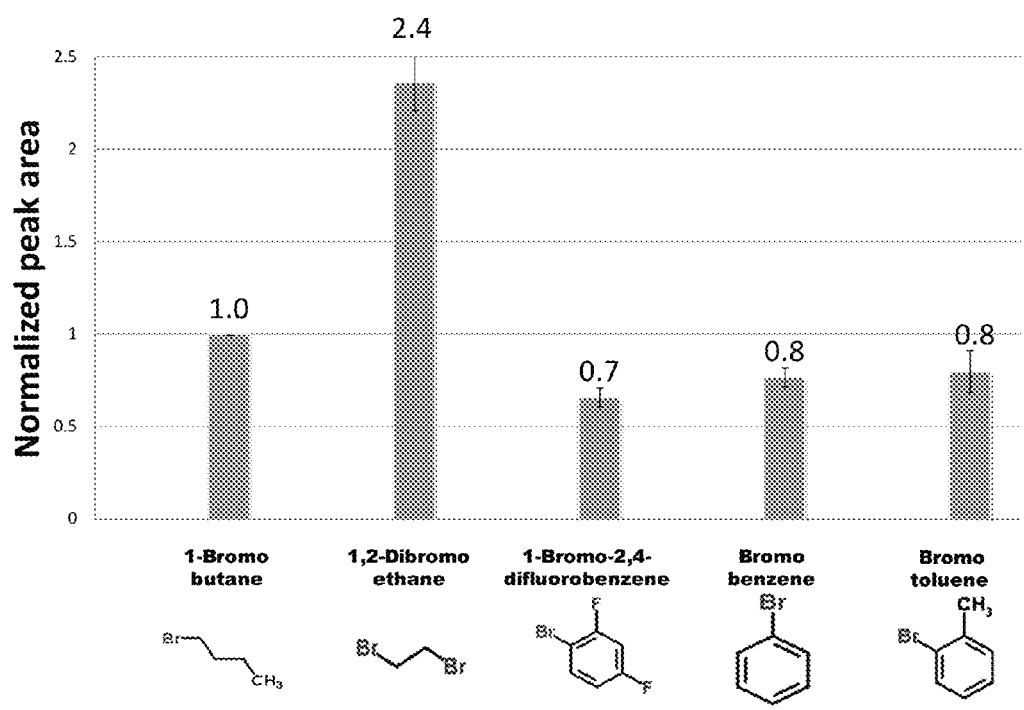
FIG. 12: Normalized peak areas for GC-PARCI-MS of brominated compounds shown in FIG. 11.

To evaluate the compound dependence of the GC-PARCI, the chromatographic peak areas are normalized to the area corresponding to 1-bromobutane and presented in FIG. 12. The data show that PARCI-MS responses for the five compounds are within 30% of ideal behavior, confirming that PARCI provides compound-independent response factors for quantification of compounds in the absence of individual standards.

The invention claimed is:

1. An apparatus for elemental mass spectrometry comprising:
   a chemical reaction interface (CRI), which comprises reactant gas plasma;
   an ionization chamber, wherein the ionization chamber is separate from and is downstream of the CRI; and
   a mass-spectrometer.

2. The apparatus of claim 1, wherein the ionization chamber comprises an electron source.

3. The apparatus of claim 1, wherein the ionization chamber comprises an ionization gas and/or a dopant molecule.

4. The apparatus of claim 3, wherein the dopant or ionization gas is acetone, toluene, benzoic acid, nitrogen ($N_2$), oxygen, ammonia ($NH_3$), air, argon (Ar) methanol, water, or a combination thereof.

5. The apparatus of claim 1, wherein the pressure in the ionization chamber is greater than about 1.0 torr.

6. The apparatus of claim 1, wherein the plasma reactant gas comprises helium (He), nitrogen ($N_2$), argon (Ar), oxygen ($O_2$), hydrogen ($H_2$), air, water or a combination thereof.

7. The apparatus of claim 1, wherein the plasma is at a pressure of between about 1.0 torr to about 50.0 torr.

8. The apparatus of claim 1, wherein the plasma is at atmospheric pressure.

9. The apparatus of claim 1, wherein the ionization chamber is at a pressure of between about 1 torr to about 50 torr.

10. The apparatus of claim 1, wherein the ionization chamber is at atmospheric pressure.

11. The apparatus of claim 1, wherein the apparatus further comprises a chromatograph.

12. The apparatus of claim 11, wherein the chromatograph is a liquid chromatograph (LC) or gas chromatograph (GC).

13. The apparatus of claim 1, wherein the plasma gas is self-contained or ignited by a Tesla coil.

14. The apparatus of claim 1, wherein the apparatus further comprises a nebulizer.

15. The apparatus of claim 14, wherein the nebulizer is a thermospray nebulizer (TSN) or a pneumatic high efficiency nebulizer (HEN).

16. The apparatus of claim 1, wherein the apparatus further comprises a means to separate an analyte from solvent.

17. The apparatus of claim 1, wherein the mass spectrometer is an atmospheric sampling mass spectrometer.

18. The apparatus of claim 1, wherein the apparatus further comprises a momentum separator.

19. A method for elemental mass spectrometric analysis of an analyte comprising:
    (1) introducing a sample comprising the analyte into a sample introduction component of a mass spectrometric system;
    (2) transporting the analyte into a chemical reaction interface (CRI) comprising a reactant gas plasma; wherein the CRI converts the analyte into one or more element specific compounds;
    (3) introducing the element specific compounds into an ionization chamber that is separate from and is downstream of the CRI thereby ionizing the element specific compounds to form charged element specific products; and
    (4) detecting the one or more charged element specific products by a mass spectrometer.

20. The method of claim 19, wherein the analyte is an organic chemical compound.

21. The method of claim 19, wherein the element specific compounds are ionized by an ionization gas, a dopant molecule, and/or an electron source.

22. The method of claim 21, wherein the dopant or ionization gas has an ionization potential less than 16.0 eV.

23. The method of claim 22, wherein the dopant or ionization gas is acetone, toluene, benzoic acid, nitrogen ($N_2$), oxygen, ammonia ($NH_3$), air, argon (Ar), methanol, water, or a combination thereof.

24. The method of claim 19, wherein the analyte comprises one or more of the compounds selected from the group consisting of an amino acid, a carbohydrate, a polypeptide, a protein, a nucleic acid, and a lipid.

25. The method of claim 19, wherein the analyte comprises one or more halogen atoms.

26. The method of claim 19, wherein the organic compound comprises one or more fluorine atoms, chlorine atoms, or bromine atoms.

27. The method of claim 19, wherein the plasma reactant gas comprises helium (He), nitrogen ($N_2$), argon (Ar), oxygen ($O_2$), hydrogen ($H_2$), air, water or a combination thereof.

28. The method of claim 19, wherein the plasma is at a pressure of between about 1.0 torr to about 50.0 torr.

29. The method of claim 19, wherein the plasma is at atmospheric pressure.

30. The method of claim 21, wherein the dopant or ionization gas has an ionization potential that is less than the ionization potential of a metastable species of carrier gas formed in the CRI.

31. The method of claim 19, wherein the charged element specific product is formed at a pressure of greater than about 1.0 torr.

32. The method of claim 19, wherein the charged element specific product is a negatively or positively charged ion.

33. The method of claim 32, wherein the charged element specific product is a negatively charged ion.

34. The method of claim 33, wherein the negatively charged element specific product contains a halogen.

35. The method of claim 34, wherein the halogen is a fluorine ion or a bromine ion.

36. The method of claim 34, wherein the plasma reactant gas comprises He.

37. The method of claim 34, wherein the plasma reactant gas consists of He.

38. The method of claim 19, wherein the mass spectrometer is an atmospheric sampling mass spectrometer.

39. The method of claim 38, wherein the chromatography is liquid chromatography (LC) or gas chromatography (GC).

40. The method of claim 39, wherein the liquid chromatography is high performance liquid chromatography (HPLC).

41. The method of claim 19, wherein the analyte is separated from the sample by chromatography.

42. A kit for modifying a mass spectrometer for plasma-assisted reaction chemical ionization comprising:
    a chemical reaction interface (CRI) comprising a plasma cavity wherein the plasma cavity comprises a plasma of a carrier gas with a reactant gas; and
    an ionization chamber, wherein the ionization chamber is separate from and is downstream from the plasma cavity.

43. The kit of claim 42, further comprising means for infusing the CRI with the reactant gas.

44. The kit of claim 42, further comprising means for introducing ionization gas or dopant into the ionization chamber.

* * * * *